(12) United States Patent
Cholette et al.

(10) Patent No.: US 8,571,684 B2
(45) Date of Patent: Oct. 29, 2013

(54) IMPLANTABLE LEAD ASSEMBLY HAVING A POSITION TRACKING SENSOR AND METHOD OF MANUFACTURING THE LEAD ASSEMBLY

(75) Inventors: Martin Cholette, Acton, CA (US); Sean Matthew Desmond, Moorpark, CA (US)

(73) Assignee: Pacesetter, Inc., Sylmar, CA (US)

( * ) Notice: Subject to any disclaimer, the term of this patent is extended or adjusted under 35 U.S.C. 154(b) by 136 days.

(21) Appl. No.: 13/099,227

(22) Filed: May 2, 2011

(65) Prior Publication Data

US 2012/0283809 A1 Nov. 8, 2012

(51) Int. Cl.
*A61N 1/00* (2006.01)

(52) U.S. Cl.
USPC ........................................................ 607/116

(58) Field of Classification Search
USPC ........................ 607/2, 115–142, 63; 600/9–15
See application file for complete search history.

(56) References Cited

U.S. PATENT DOCUMENTS

| 2004/0097805 A1 | 5/2004 | Verard et al. |
| 2009/0118610 A1 | 5/2009 | Karmarkar et al. |
| 2010/0057157 A1* | 3/2010 | Govari et al. ................... 607/19 |
| 2011/0276104 A1* | 11/2011 | Ameri et al. .................... 607/11 |

FOREIGN PATENT DOCUMENTS

| EP | 1504713 B1 | 3/2008 |
| EP | 2062530 A2 | 5/2009 |
| EP | 2062530 A3 | 8/2009 |
| WO | 2007064739 A2 | 6/2007 |
| WO | 2007064739 A3 | 12/2007 |
| WO | 2010014420 A1 | 2/2010 |

* cited by examiner

*Primary Examiner* — Scott Getzow

(57) ABSTRACT

A lead assembly of an implantable medical device includes an elongated body, electrodes on the body, and a tracking sensor located in the body. The body extends between a connector end and a leading end and has conductors disposed in the body. The connector end of the body includes terminals coupled with the conductors. The electrodes disposed on the body can be located at or near an anatomy of interest in a patient and are conductively coupled with the terminals of the body by the conductors. The electrodes are configured to sense electric activity of the anatomy of interest and/or deliver stimulus pulses to the anatomy of interest. The tracking sensor is conductively coupled with the terminals of the body by the conductors. The tracking sensor generates an electric position signal representative of a position of the tracking sensor in the heart when the body is in the patient.

22 Claims, 9 Drawing Sheets

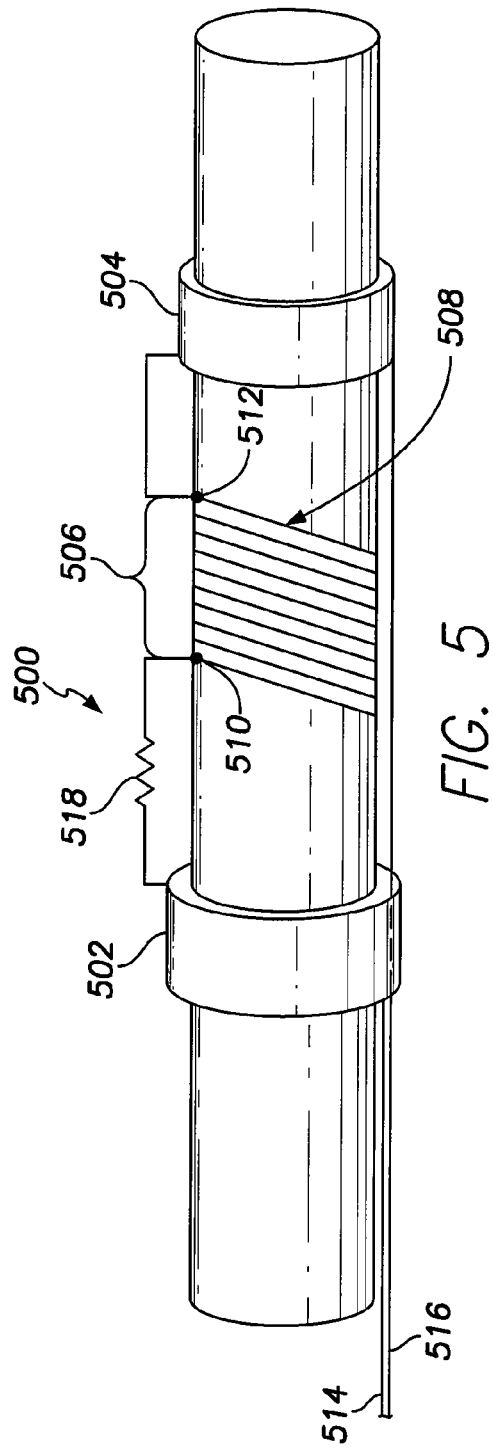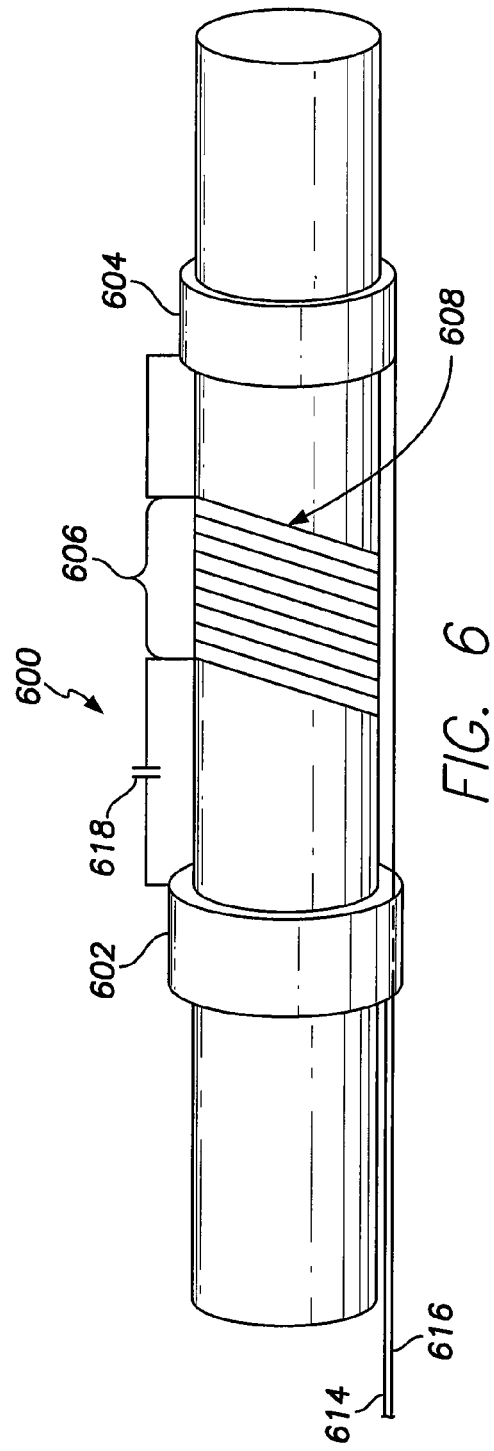

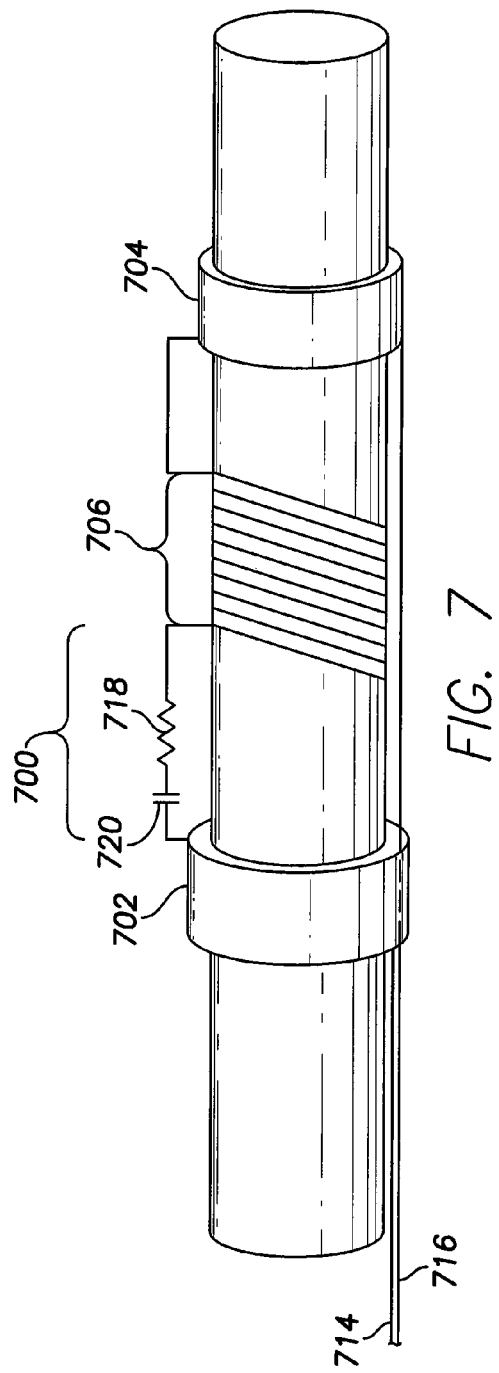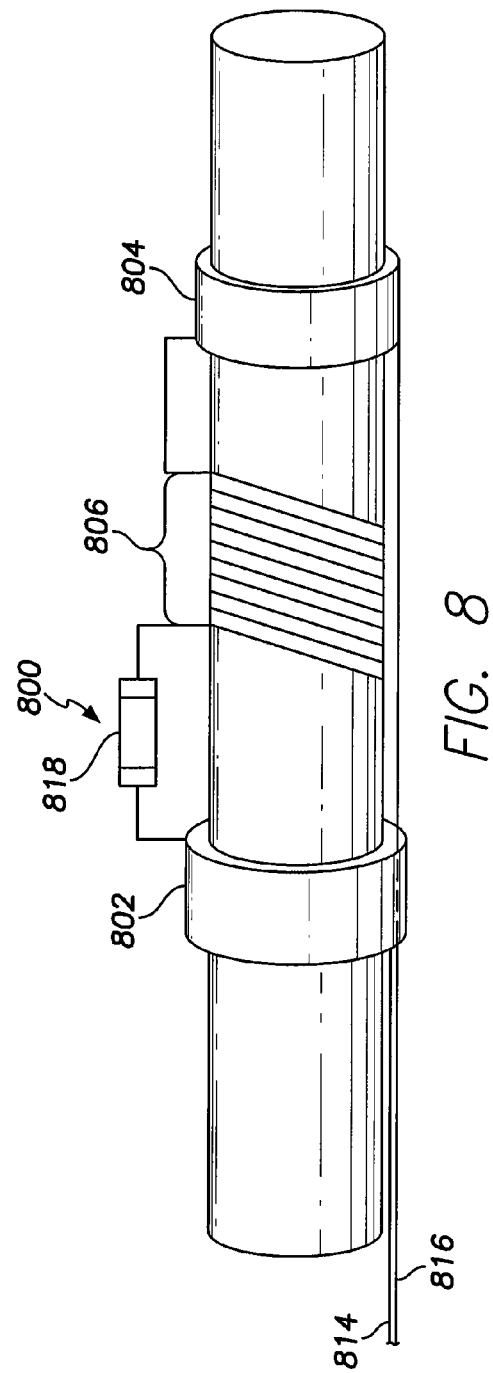

IMPLANTABLE LEAD ASSEMBLY HAVING A POSITION TRACKING SENSOR AND METHOD OF MANUFACTURING THE LEAD ASSEMBLY

FIELD OF THE INVENTION

One or more embodiments of the subject matter described herein generally relate to lead assemblies for implantable medical devices.

BACKGROUND OF THE INVENTION

Implantable lead assemblies can be used with implantable pulse generators (such as neurostimulators, pacemakers, defibrillators, or implantable cardioverter defibrillators (ICD)) to sense electric signals of the heart, neuro signals from the body, and/or deliver stimulus pulses to the heart or another anatomy. A lead assembly is implanted on, near or into the heart or another anatomy by inserting a distal leading end of the assembly into a vein that extends to the heart or near other anatomy. The lead assembly may be implanted into one or more chambers of the heart.

Some known lead assemblies are implanted into the heart or other anatomy using angiography. Angiography is an imaging procedure that visualizes blood vessels within a body. Typically, a radio-opaque contrast agent is injected into a blood vessel and an x-ray imaging modality (e.g., fluoroscopy) generates images of the blood vessel. Angiography also can be used to generate images of the lead assembly as the lead assembly is implanted in the body.

Angiography is not without problems. Angiography can cause cardiac arrhythmia during the implant procedure. The contrast agent may damage a patient's kidneys and/or lead to blood clots. Moreover, some patients may have an allergic reaction to the contrast agent. As the age of the patient increases, the risk of encountering one or more of these problems also increases.

A need exists for the ability to monitor the location of an implantable lead assembly as the lead assembly is implanted into a body, without the complications or risks associated with angiography.

BRIEF SUMMARY OF THE INVENTION

A lead assembly of an implantable medical device is disclosed herein. The lead assembly includes an elongated tubular body, one or more electrodes disposed on the body, and a position tracking sensor located in the body. The body extends between a proximal connector end and a distal leading end and has one or more elongated conductors disposed in the body. The connector end of the body includes one or more conductive terminals coupled with the conductors. The electrodes disposed on the body are configured to be located at or near an anatomy of interest in a patient and are conductively coupled with one or more of the terminals of the body by one or more of the conductors. The one or more electrodes are configured to sense electric activity of the anatomy of interest and/or deliver stimulus pulses to the anatomy of interest. The tracking sensor is conductively coupled with one or more of the terminals of the body by one or more of the conductors. The tracking sensor generates an electric position signal representative of a position of the tracking sensor when the body is in the patient.

In another embodiment, another lead assembly of an implantable medical device is provided. The lead assembly includes an elongated tubular body, first and second electrodes disposed on the body, and a position tracking sensor located in the body. The body extends between a proximal connector end and a distal leading end. The body includes first and second elongated conductors disposed in the body and the connector end of the body having first and second conductive terminals coupled with the first and second conductors, respectively. The first and second electrodes are configured to be located at or near an anatomy of interest in a patient. The first and second electrodes are conductively coupled with the first and second terminals, respectively, by the first and second conductors. The first and second electrodes are configured to sense electric activity of the anatomy of interest and/or deliver stimulus pulses to the anatomy of interest. The tracking sensor is disposed in the body and is conductively coupled with the first and second electrodes. The tracking sensor is configured to generate an electric position signal that represents a position of the tracking sensor in the patient when the body is in the patient. The tracking sensor conductively couples the first and second electrodes when the body is implanted into the body.

In another embodiment, a method of manufacturing a lead assembly of an implantable medical device is provided. The method includes providing an elongated tubular body extending between a proximal connector end and a distal leading end. The body has first and second elongated conductors disposed in the body. The connector end of the body includes first and second conductive terminals coupled with the first and second conductors, respectively. The method also includes positioning first and second electrodes on the body that are configured to be located at or near an anatomy of interest in the patient. The first and second electrodes are conductively coupled with the first and second terminals, respectively, by the first and second conductors. The first and second electrodes are configured to sense electric activity of the anatomy of interest and/or deliver stimulus pulses to the anatomy of interest. The method further includes providing a position tracking sensor in the body that conductively coupled with the first and second electrodes. The tracking sensor is configured to generate an electric signal that represents a position of the tracking sensor in the heart when the tracking sensor is exposed to an external magnetic field. The tracking sensor conductively couples the first and second electrodes when the body is implanted into the patient.

While multiple embodiments are disclosed, still other embodiments of the described subject matter will become apparent to one of ordinary skill in the art from the following Detailed Description, which shows and describes illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

BRIEF DESCRIPTION OF THE DRAWINGS

FIG. 5 is a circuit diagram of one embodiment of a resistive electric isolation component and a tracking sensor.

FIG. 6 is a circuit diagram of a capacitive electric isolation component and a tracking sensor in accordance with another embodiment.

FIG. 7 is a circuit diagram of a hybrid electric isolation component and a tracking sensor in accordance with another embodiment.

FIG. 8 is a circuit diagram of a fused electric isolation component and a tracking sensor in accordance with another embodiment.

DETAILED DESCRIPTION

One or more embodiments described herein provide an implantable lead assembly of a medical device that includes a position tracking sensor and one or more pacing and/or sensing electrodes. The tracking sensor can be used to identify a location of the lead assembly inside a patient as the lead assembly is implanted into the patient. For example, the tracking sensor may generate electric signals representative of a position of the tracking sensor when the tracking sensor is exposed to an external magnetic field. Once the lead assembly is implanted, the electrodes may be used to deliver stimulus pulses to the body and/or sense electric activity or signals of the body. The tracking sensor may be positioned within the lead assembly such that the tracking sensor remains in the body after the lead assembly is implanted. In one embodiment, the tracking sensor is disposed within a lead assembly that is implanted into a heart of the patient and that is used to deliver pacing or stimulus pulses to the heart and/or sense cardiac signals of the heart. In another embodiment, the tracking sensor is disposed within a lead assembly that is implanted into or near other anatomy of the patient and that is used to deliver stimulus pulses to the body and/or sense electric signals of the body. For example, the tracking sensor may be located within a lead assembly connected to a neuromodulation or neurostimulation device.

Figure 1:
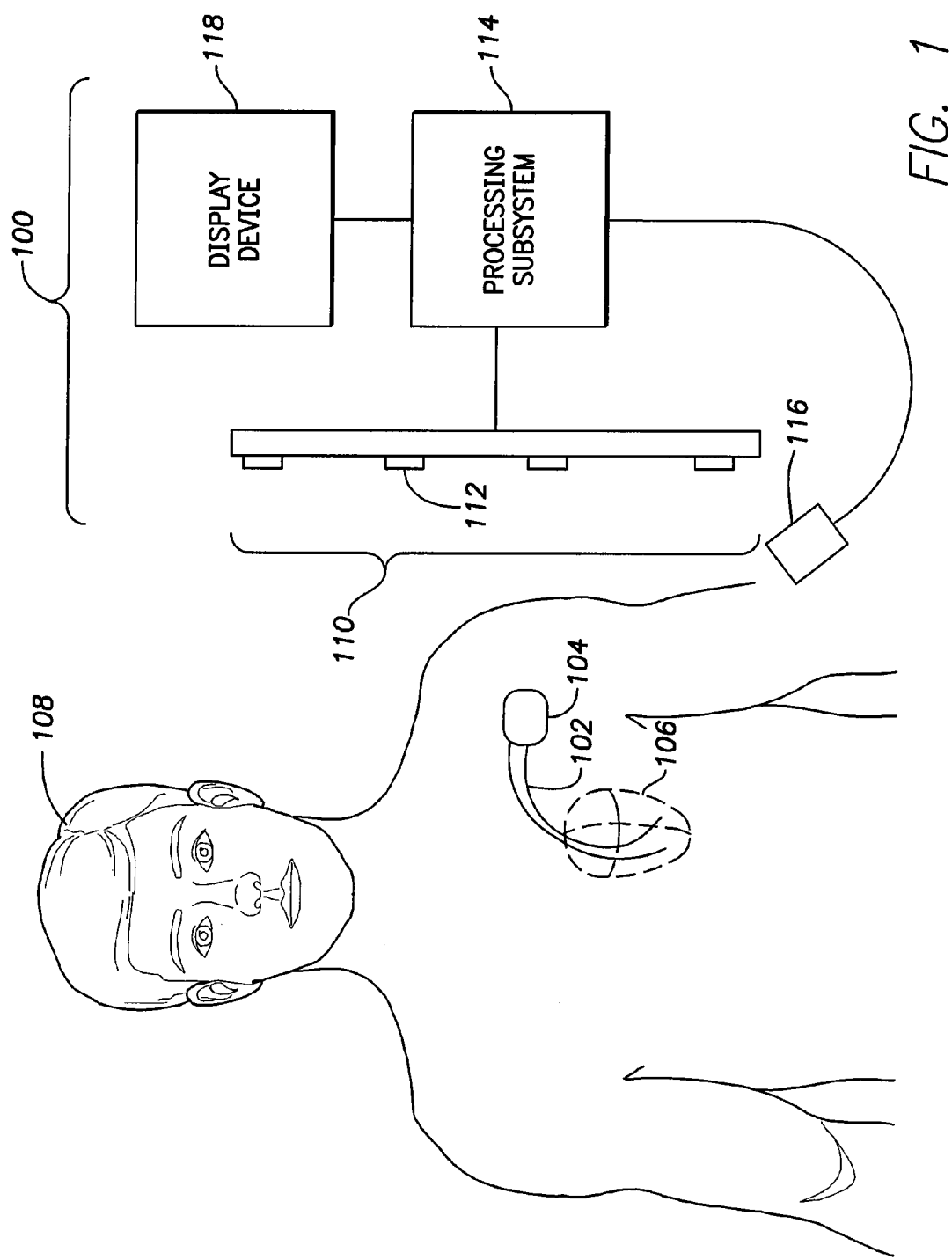
FIG. 1 is a perspective view of one embodiment of a tracking system.

FIG. 1 is a perspective view of one embodiment of a tracking system 100. The tracking system 100 can be used to monitor and/or display a location of an implantable lead assembly 102 of a medical device 104 in an anatomy 106 of a patient 108. The discussion herein focuses on the implant of the lead assembly 102 into a heart of the patient 108. Alternatively, the lead assembly 102 may be implanted into another anatomy of the patient 108, such as near the spinal column of the patient 108. In one embodiment, the lead assembly 102 is partially implanted into the anatomy 106 to deliver stimulus pulses (such as pacing or defibrillation pulses delivered to a heart) to the anatomy 106 and/or sense electric signals of the anatomy 106 (e.g., cardiac signals). Alternatively, the lead assembly 102 is implanted into the body of the patient 108 to sense electric activity and/or deliver stimulus pulses to another anatomy of the patient 108, such as the nervous system of the patient 108. The IMD 104 generates the stimulus pulses and/or includes a processor to analyze the sensed electric signals. The IMD 104 may be a pacemaker, defibrillator, implantable cardiac defibrillator (ICD), neurostimulators, or neuromodulator. The IMD 104 receives the lead assembly 102 to establish conductive pathways between the IMD 104 and the lead assembly 102 for communication of the stimulus pulses and/or sensed electric signals between the IMD 104 and the lead assembly 102. When the IMD 104 is a neurostimulator or neuromodulator, the lead assembly 102 is located at or near another anatomy of interest (e.g., an anatomy other than the heart). While two lead assemblies 102 are shown in FIG. 1, alternatively a different number of lead assemblies 102 may be provided.

As described below, the lead assembly 102 includes a position tracking sensor 300 (shown in FIG. 3), such as a conductive coil, that generates electric position signals when the tracking sensor 300 is exposed to an external magnetic field. Alternatively, the tracking sensor 300 may generate a magnetic field that is served to identify the position of the tracking sensor. The tracking system 100 includes an array 110 comprised of a plurality of transmitter coils 112. The transmitter coils 112 generate magnetic fields into the volume around the anatomy 106. Alternatively, components other than coils may be used to generate the magnetic fields around the anatomy 106. The array 110 is driven or controlled by a processing subsystem 114 of the tracking system 100.

Prior to implanting the lead assembly 102 into the anatomy 106, the lead assembly 102 is communicatively coupled with the tracking system 100. In the illustrated embodiment, the tracking system 100 includes a connector interface 116 that mates with the lead assembly 102. The connector interface 116 may be a receptacle that receives one end of the lead assembly 102 to conductively couple the tracking sensor 300 (shown in FIG. 3) in the lead assembly 102 with the tracking system 100. The magnetic fields generated by the coils 112 in the array 110 induce electric current in the tracking sensor 300. This electric current is conveyed through the lead assembly 102 to the tracking system 100 as a position signal that represents the position of the tracking sensor 300 within the magnetic field. The position signal is communicated to the tracking system 100 via the connector interface 116 as the tracking sensor 300 moves through the anatomy 106.

The processing subsystem 114 receives the position signal and analyzes the position signal to determine the location of the tracking sensor 300 (shown in FIG. 3) in the anatomy 106. The processing subsystem 114 communicates the location of the tracking sensor 300 to a display device 118, which can visually represent the location of the tracking sensor 300 and/or the lead assembly 102 relative to the anatomy 106 to an operator. For example, the display device 118 may present an image of the anatomy 106 (or a template image of a heart) and superimpose an icon or other visual representation of the tracking sensor 300 and/or lead assembly 102 on the image of the anatomy 106. The operator of the tracking system 100 can manipulate the lead assembly 102 based on the presentation on the display device 118.

Once the lead assembly 102 is implanted into the anatomy 106 (such as in a desired or destination location), the lead assembly 102 can be decoupled from the connector interface 116 of the tracking system 100. The lead assembly 102 may then be coupled with the IMD 104, as shown in FIG. 1. The lead assembly 102 senses electric signals of the anatomy 106 and communicates the electric signals to the IMD 104 and/or delivers stimulus pulses to the anatomy 106 from the IMD 104. The electric signals represent electric activity of the patient 108, such as cardiac signals, neuro signals, and the like.

Figure 2:
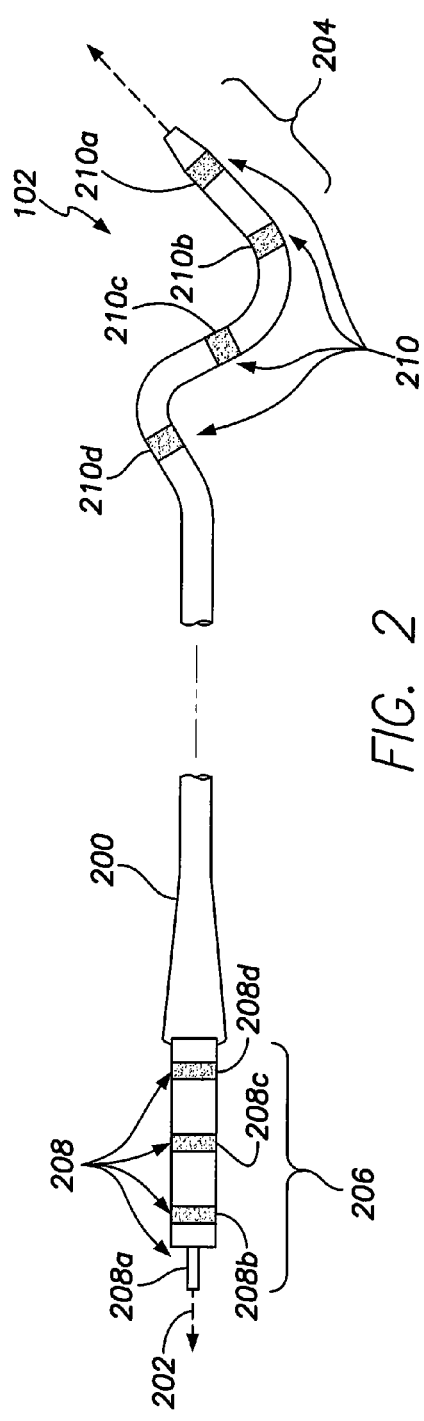
FIG. 2 is a perspective view of one embodiment of an implantable lead assembly shown in FIG. 1.

FIG. 2 is a perspective view of one embodiment of the lead assembly 102. The lead assembly 102 includes an elongated tubular body 200 extending along a center axis 202 from a distal leading end 204 to a proximal connector end 206. As shown in FIG. 2, the center axis 202 may include twists, turns, or undulations, and generally extend along a non-linear path. The connector end 206 includes several conductive terminals 208, such a pin contact and three ring contacts. The terminals 208 are generally referred to by the reference number 208 and are individually referred to by the reference number 208A, 208B, 208C, or 208D, as shown in FIG. 2. While four terminals 208 are shown, including a single pin terminal 208A and three ring terminals 208B, 208C, and 208D, alternatively, a different number of terminals 208 (e.g., pin terminals 208A and/or ring terminals 208B, 208C, 208D) may be provided.

The leading end 204 of the lead assembly 102 includes several conductive electrodes 210. The electrodes 210 are generally referred to by the reference number 210 and are individually referred to by the reference number 210A, 210B, 210C, or 210D. In the illustrated embodiment, the electrodes 210 include a tip electrode 210A, and three ring electrodes 210B, 210C, 210D. While four electrodes 210 are shown, alternatively, a different number and/or type of electrodes 210 may be provided. The electrodes 210 are disposed along an outer surface of the body 200 such that the electrodes 210 engage the anatomy 106 (shown in FIG. 1) when the lead assembly 102 is implanted into the anatomy 106. The electrodes 210 sense electric signals of the anatomy 106 and/or deliver stimulus pulses to the anatomy 106.

The electrodes 210 are electrically coupled with the terminals 208 by elongated conductors 306 (shown in FIG. 3) that extend through the body 200 of the lead assembly 102 from the leading end 204 to the connector end 106. When the connector end 206 is inserted into the IMD 104 (shown in FIG. 1), the terminals 208 are conductively coupled with the IMD 104 and the conductors 306 provide conductive pathways through the lead assembly 102. Electric signals sensed by the electrodes 210 are communicated to the IMD 104 and/or stimulus pulses are delivered to the electrodes 210 via the conductors 306 and the terminals 208.

Figure 3:
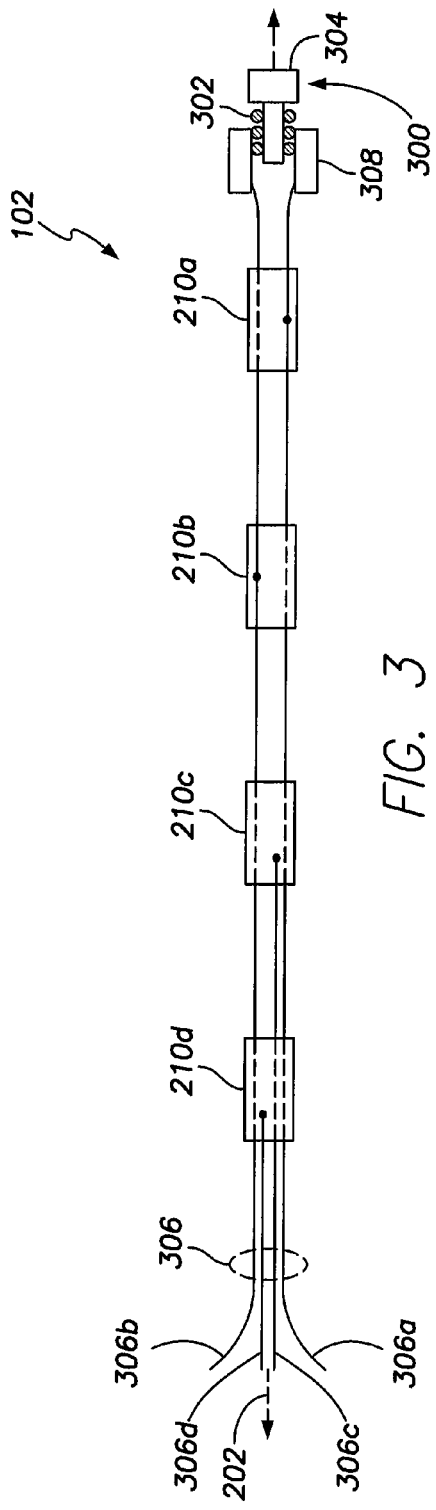
FIG. 3 is one embodiment of a circuit diagram of electronic components of the lead assembly shown in FIG. 1.

FIG. 3 is one embodiment of a circuit diagram of the electronic components of the lead assembly 102. The circuit diagram illustrates several circuits in the lead assembly 102 that are used to communicate electric signals and/or stimulus pulses between the IMD 104 (shown in FIG. 1) and the electrodes 210, as well as position signals between the tracking sensor 300 and the tracking system 100 (shown in FIG. 1).

In the illustrated embodiment, the tracking sensor 300 includes a conductive coil 302 that is helically wrapped around the center axis 202 of the lead assembly 102. The coil 302 may be wrapped around a core body 304, such as a ferrite core. An electric current is induced in the coil 302 when the coil 302 is exposed to an external magnetic field, such as the magnetic fields generated by the tracking system 100 (shown in FIG. 1). This induced current represents the position signal generated by the tracking sensor 300. Alternatively, the coil 302 may generate a magnetic field by conveying electric current through the coil 302. The array 110 of the tracking system 100 shown in FIG. 1 may sense the magnetic field to determine a position of the coil 302.

The lead assembly 102 includes four elongated conductors 306 in the embodiment shown in FIG. 3. The elongated conductors 306 are collectively referred to by the reference number 306 and are individually referred to by the reference numbers 306A, 306B, 306C, or 306D. While four conductors 306 are shown, alternatively, a different number of conductors 306 may be provided. The conductors 306 may be linear conductive bodies, such as filars, or may be conductive bodies that are elongated and helically wrapped around the center axis 202 in the shape of a coil. The representation of the conductors 306 as linear bodies in FIG. 3 may apply to coiled conductors as well.

The electrodes 210 are conductively coupled with the conductors 306. The conductors 306 are conductively coupled with the terminals 208. As shown in FIG. 3, the conductor 306D is conductively coupled with the terminal 208D and the electrode 210D. The conductor 306C is conductively coupled with the terminal 208C and the electrode 210C. The conductors 306C and 306D are not conductively coupled with any other electrode 210A or 210B or the tracking sensor 300 in the illustrated embodiment. Electric signals and/or stimulus pulses are separately communicated between the IMD 104 and the electrodes 210C and 210D through the conductors 306C and 306D.

The conductor 306B is conductively coupled with the terminal 208B and the electrode 210B. The conductor 306A is conductively coupled with the terminal 208A and the electrode 210A. The tracking sensor 300 and one or more of the electrodes 210 are conductively coupled with a common conductor 306. For example, the coil 302 of the tracking sensor 300 and the electrode 210A are conductively coupled with the same conductor 306A. As another example, the coil 302 and the electrode 210B are conductively coupled with the same conductor 306B. As a result, the tracking sensor 300 can be conductively coupled in series with the electrodes 210A, 210B by the conductors 306A, 306B. In the illustrated embodiment, the tracking sensor 300 is joined in series with the electrodes 210A, 210B and is located between the electrodes 210A, 210B. As a result, the electrodes 210A, 210B can be conductively coupled by the conductors 306A, 306B and the tracking sensor 300.

One or more electric isolation components 308 are disposed in series with the electrodes 210A, 210B and the tracking sensor 300. For example, an electric isolation component 308 may be conductively coupled with the electrodes 210A, 210B and the tracking sensor 300 by the conductors 306A, 306B. As shown in FIG. 3, the isolation component 308 can be disposed between the tracking sensor 300 and each of the electrodes 210A, 210B.

Figure 4:
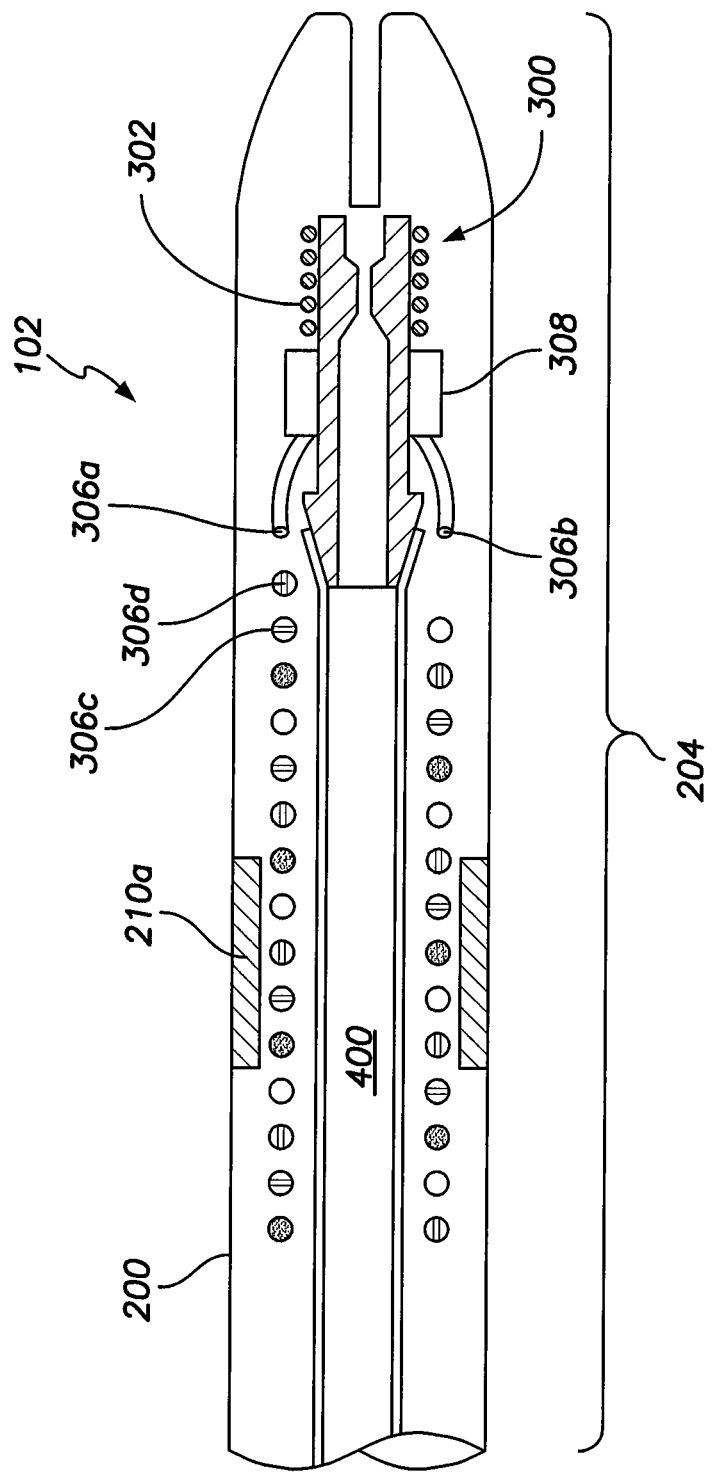
FIG. 4 is a cross-sectional view of a leading end of the lead assembly shown in FIG. 1 in accordance with one embodiment.

FIG. 4 is a cross-sectional view of the leading end 204 of the lead assembly 102 of FIG. 3 in accordance with one embodiment. The body 200 of the lead assembly 102 defines a central lumen 400 extending along the length of the body 200. One or more guidewires, stylets, and the like (not shown) may be disposed within the central lumen 400. The conductors 306 are helically wrapped around the central lumen 400 in the illustrated embodiment. The tracking sensor 300 may be located within the body 200 in a location that is distal to the electrodes 210. For example, the tracking sensor 300 may be located farther from the connector end 206 (shown in FIG. 2) of the body 200 than the electrodes 210. Positioning the tracking sensor 300 distal to the electrodes 210 can allow the tracking system 100 to more accurately monitor the location of the distal tip or end of the body 200. Alternatively, the tracking sensor 300 may be located between or among the electrodes 210. For example, the tracking sensor 300 may be disposed between the electrode 210A and the electrode 210B.

The isolation component 308 may be disposed in series with and between the conductor 306A and the tracking sensor 300. For example, the conductor 306A can be coupled with the isolation component 308 and the isolation component 308 can be coupled with one end of the coil 302. The conductor 306B can be coupled with the electric isolation component 308, which is coupled with the opposite end of the coil 302.

In operation, when the tracking system 100 is used to monitor the location of the tracking sensor 300 in the anatomy 106, the isolation component 308 allows position signals generated by the tracking sensor 300 to be conveyed along the conductors 306A, 306B to the tracking system 100. For example, the isolation component 308 may permit the position signals to pass through the isolation component 308, along the conductors 306A, 306B, and to the terminals 208A, 208B of the lead assembly 102 to the connector interface 116 of the tracking system 100.

After the lead assembly 102 is implanted into the anatomy 106 and the lead assembly 102 is coupled with the IMD 104, the isolation component 308 may prevent electric current from flowing between the electrode 210A and the electrode 210B, and between the conductor 306A and the conductor 306B. For example, the isolation component 308 may block stimulus pulses delivered from the IMD 104 and along the conductor 306B to the electrode 210B from flowing through the tracking sensor 300 to the electrode 210A and the conductor 306A. Similarly, the isolation component 308 may prevent stimulus pulses delivered along the conductor 306A to the electrode 210A from flowing through the tracking sensor 300 to the electrode 210B and the conductor 306B. In another example, the isolation component 308 may prevent electric signals sensed by the electrode 210B from being conducted through the tracking sensor 300 to the electrode 210A and the conductor 306A. Similarly, the isolation component 308 may prevent electric signals sensed by the electrode 210A from being conducted through the tracking sensor 300 to the electrode 210B and the conductor 306B.

FIG. 5 is a circuit diagram of one embodiment of a resistive electric isolation component 500 and a tracking sensor 506. The isolation component 500 may represent the isolation component 308 (shown in FIG. 3) and the tracking sensor 506 may represent the tracking sensor 300 (shown in FIG. 3). In the circuit diagram shown in FIG. 5, the isolation component 500 is conductively coupled in series with the tracking sensor 506, a first electrode 502, and a second electrode 504. The first electrode 502 may represent the electrode 210A and the second electrode 504 may represent the electrode 210B. Alternatively, the first electrode 502 may represent the electrode 210B and the second electrode 504 may represent the electrode 210A.

The first electrode 502 is conductively coupled with a first elongated conductor 514 (e.g., the conductor 306A shown in FIG. 3) and the second electrode 504 is conductively coupled with a second elongated conductor 516 (e.g., the conductor 306B shown in FIG. 3). The tracking sensor 506 includes a conductive coil 508 that may be similar to the coil 302 of the tracking sensor 300. The coil 508 extends between opposite ends 510, 512, with one end 510 conductively coupled with the isolation component 500 and the opposite end 512 conductively coupled with the second electrode 504. As a result, the isolation component 500 may be conductively coupled in series with the electrodes 210A and 210B (shown in FIG. 2) and with the conductors 306A and 306B (shown in FIG. 3). A conductive pathway may extend through the first conductor 514, the first electrode 502, the isolation component 500, the tracking sensor 506, the second electrode 504, and the second conductor 516.

In the illustrated embodiment, the isolation component 500 includes a resistive element 518. The resistive element 518 may be a resistor having an electric resistance characteristic that is relatively large. For example, the resistive element 518 may have a resistance that is greater than the resistance of any of the first electrode 502, the second electrode 504, the coil 508, the conductor 514, or the conductor 516. In one embodiment, the resistance of the resistive element 518 is at least 20 kilo Ohms or greater. Alternatively, the resistive element 518 may have a different resistance. The resistance of the resistive element 518 can exceed the resistance of the myocardium or other biological tissue to which the electrode 502 and/or the electrode 504 is in contact. For example, each of the electrodes 502, 504 may be engaged with areas of the anatomy 106 that have a lower resistance than the resistive element 518. The resistance of the resistive element 518 may be at least one or two orders of magnitude larger than the resistance of the anatomy 106.

In operation, when the lead assembly 102 is implanted into the anatomy 106 and the tracking system 100 is monitoring the location of the tracking sensor 506, the position signals generated by the tracking sensor 506 may be conducted through the isolation component 500 and the first electrode 502 to the first conductor 514 and through the second electrode 504 to the second conductor 516. The tracking system 100 receives the position signals from the first and second conductors 514, 516.

Once the lead assembly 102 is implanted in the anatomy 106 and the location of the tracking sensor 506 is completed, the resistive element 518 of the isolation component 500 blocks or prevents electric current from flowing between the first electrode 502 and the second electrode 504 and between the first conductor 514 and the second conductor 516. For example, stimulus pulses that are delivered along the first conductor 514 to the first electrode 502 are conducted to the anatomy 106 instead of through the resistive element 518 of the isolation component 500 to the second electrode 504 or second conductor 516. Similarly, stimulus pulses that are delivered along the second conductor 516 to the second electrode 504 are conducted to the anatomy 106 instead of through the resistive element 518 of the isolation component 500 to the first electrode 502 or the first conductor 514. The stimulus pulses flow to the anatomy 106 instead of to another electrode 502, 504 or conductor 514, 516 due to the lower resistance of the anatomy 106. The conductive pathway that extends from the first conductor 514 to the first electrode 502 and to the anatomy 106 has a lower resistance than the conductive pathway that extends through the isolation component 500 to the second electrode 504. Similarly, the conductive pathway that extends from the second conductor 516 to the second electrode 504 and to the anatomy 106 has a lower resistance than the conductive pathway that extends through the isolation component 500 to the first electrode 502.

In another example, electric signals that are sensed by the first electrode 502 or the second electrode 504 are conducted through the first conductor 514 or the second conductor 516, respectively, to the IMD 104 instead of through the isolation component 500 to the other electrode 502 or 504 or to the other conductor 514 or 516. The electric signals flow to the IMD 104 instead of to another electrode 502, 504 or conductor 514, 516 due to the lower resistance of the pathway that extends to the IMD 104 relative to the pathway that extends through the isolation component 500.

FIG. 6 is a circuit diagram of a capacitive electric isolation component 600 and a tracking sensor 606 in accordance with another embodiment. The isolation component 600 may represent the isolation component 308 (shown in FIG. 3) and the tracking sensor 606 may represent the tracking sensor 300 (shown in FIG. 3). In the circuit diagram shown in FIG. 6, the isolation component 600 is conductively coupled in series with the tracking sensor 606, a first electrode 602, and a second electrode 604. The first electrode 602 may represent the electrode 210A and the second electrode 604 may represent the electrode 210B. Alternatively, the first electrode 602 may represent the electrode 210B and the second electrode 604 may represent the electrode 210A.

The first electrode 602 is conductively coupled with a first elongated conductor 614 (e.g., the conductor 306A shown in FIG. 3) and the second electrode 604 is conductively coupled with a second elongated conductor 616 (e.g., the conductor 306B shown in FIG. 3). The tracking sensor 606 includes a conductive coil 608 that may be similar to the coil 302 of the tracking sensor 300. The coil 608 is conductively coupled with the isolation component 600 and the second electrode 604. As a result, the isolation component 600 may be conductively coupled in series with the electrodes 210A and 210B and with the conductors 306A and 306B.

In the illustrated embodiment, the isolation component 600 includes a capacitive element 618. The capacitive element 618 may be a capacitor having an inductance that permits the position signals to be conducted through the capacitive element 618 and along the conductors 614, 616 from the coil 608 to the tracking system 100 but that blocks other current (e.g., stimulus pulses and/or electric signals) from flowing through the capacitive element 618 and between the electrodes 602, 604 or between the conductors 614, 616. For example, the capacitive element 618 can have an impedance (Z) that varies based on the frequency of the external magnetic field to which the capacitive element 618 is exposed and/or of the current flowing through the conductors 614, 616. The impedance (Z) of the capacitive element 618 may decrease when the capacitive element 618 is exposed to the external magnetic fields generated by the tracking system 100 and/or increase when the capacitive element 618 is removed from or not exposed to the external magnetic fields. The impedance (Z) may decrease by at least one or two orders of magnitude when the capacitive element 618 is exposed to the external magnetic fields. In one embodiment, the tracking system 100 generates magnetic fields having a frequency of approximately 10 kHz and the capacitive element 618 has an impedance (Z) that is tuned to be relatively low when exposed to magnetic fields of approximately 10 kHz.

The impedance (Z) of the capacitive element 618 may be larger than the impedance (Z) of any of the first electrode 502, the second electrode 504, the coil 508, the conductor 514, or the conductor 516 when the capacitive element 618 is not exposed to the external magnetic fields of the tracking system 100. The impedance (Z) of the capacitive element 618 can exceed the impedance (Z) of the myocardium or other biological tissue to which the electrode 602 and/or the electrode 604 is in contact when the capacitive element 618 is not exposed to the external magnetic fields of the tracking system 100.

In operation, when the lead assembly 102 is implanted into the anatomy 106 and the tracking sensor 606 is exposed to a magnetic field generated by the tracking system 100, the impedance (Z) of the isolation component 600 decreases. As a result, the position signals generated by the tracking sensor 606 may be conducted through the isolation component 600 and the first electrode 602 to the first conductor 614 and through the second electrode 604 to the second conductor 616. The tracking system 100 receives the position signals from the first and second conductors 614, 616.

Once the lead assembly 102 is implanted in the anatomy 106 and the tracking system 100 stops generating the magnetic fields, the impedance (Z) of the capacitive element 618 of the isolation component 600 increases. As a result, the capacitive element 618 blocks or prevents electric current from flowing between the first electrode 602 and the second electrode 604 and between the first conductor 614 and the second conductor 616. For example, stimulus pulses that are delivered along the first conductor 614 to the first electrode 602 are conducted to the anatomy 106 instead of through the capacitive element 618 of the isolation component 600 to the second electrode 604 or second conductor 616. Similarly, stimulus pulses that are delivered along the second conductor 616 to the second electrode 604 are conducted to the anatomy 106 instead of through the capacitive element 618 to the first electrode 602 or the first conductor 614.

The stimulus pulses flow to the anatomy 106 instead of to another electrode 602, 604 or conductor 614, 616 due to the lower impedance of the anatomy 106 relative to the impedance of the capacitive element 618. The conductive pathway that extends from the first conductor 612 to the first electrode 602 and to the anatomy 106 has a lower impedance than the conductive pathway that extends through the isolation component 600 to the second electrode 604 when the capacitive element 618 is not exposed to the external magnetic fields of the tracking system 100. Similarly, the conductive pathway that extends from the second conductor 614 to the second electrode 604 and to the anatomy 106 has a lower impedance than the conductive pathway that extends through the isolation component 600 to the first electrode 602 when the isolation component 600 is not exposed to external magnetic fields of the tracking system 100.

In another example, electric signals that are sensed by the first electrode 602 or the second electrode 604 are conducted through the first conductor 614 or the second conductor 616, respectively, to the IMD 104 instead of through the isolation component 600 to the other electrode 602 or 604 or to the other conductor 614 or 616 when the isolation component 600 is not exposed to the external magnetic fields. The electric signals flow to the IMD 104 due to the lower impedance of the pathway that extends to the IMD 104 relative to the pathway that extends through the isolation component 600.

FIG. 7 is a circuit diagram of a hybrid electric isolation component 700 and a tracking sensor 706 in accordance with another embodiment. The isolation component 700 may represent the isolation component 308 (shown in FIG. 3) and the tracking sensor 706 may represent the tracking sensor 300 (shown in FIG. 3). Similar to the isolation components 308, 500, 600 (shown in FIGS. 3, 5, and 6), the isolation component 700 is conductively coupled in series with the tracking sensor 706, a first electrode 702, a second electrode 704, a first conductor 714, and a second conductor 716.

The isolation component 700 includes both a resistive element 718 and a capacitive element 720 joined in series with each other and with the electrodes 702, 704. Similar to the resistive element 518 (shown in FIG. 5), the resistive element 718 may have a resistance that is relatively large relative to the electrodes 702, 704, conductors 714, 716, and the anatomy 106. As described above, the resistance of the resistive element 718 is sufficiently large that stimulus pulses from the IMD 104 are conducted to the anatomy 106 rather than through the resistive element 718 and electric signals are conducted to the IMD 104 rather than through the resistive element 718.

Similar to the capacitive element 618 (shown in FIG. 6), the capacitive element 720 may have an impedance (Z) that significantly decreases when the capacitive element 720 is exposed to an external magnetic field generated by the tracking system 100 and increases when the capacitive element 720 is not exposed to the magnetic field. As described above, the decreased impedance (Z) of the capacitive element 720 allows position signals to be conducted to the tracking system 100. The increased impedance (Z) of the capacitive element 720 can cause stimulus pulses from the IMD 104 to be conducted to the anatomy 106 and electric signals to be conducted to the IMD 104 rather than through the capacitive element 720.

The combination of the resistive element 718 and the capacitive element 720 in the isolation component 700 can reduce the amount of electric current that passes, or "leaks," between the electrodes 702, 704. For example, the relatively large resistance of the resistive element 718 can reduce or eliminate the stimulus pulses from passing through the isolation component 700, but may be unable to eliminate or completely block all electric signals from passing through the isolation component 700. The capacitive element 720 can reduce or eliminate the electric signals from passing through the isolation component 700. As a result, the combination of the resistive element 718 and the capacitive element 720 may block or eliminate stimulus pulses and electric signals from passing through the isolation component 700 and between the electrodes 702, 702 and between the conductors 714, 716.

FIG. 8 is a circuit diagram of a fused electric isolation component 800 and a tracking sensor 806 in accordance with another embodiment. The isolation component 800 may represent the isolation component 308 (shown in FIG. 3) and the tracking sensor 806 may represent the tracking sensor 300 (shown in FIG. 3). Similar to the isolation components 308, 500, 600, 700 (shown in FIGS. 3, 5, 6, and 7), the isolation component 800 is conductively coupled in series with the tracking sensor 806, a first electrode 802, a second electrode 804, a first conductor 814, and a second conductor 816.

The isolation component 800 includes an overcurrent protection fuse 818 that is disposed between, and conductively coupled in series with, the electrodes 802, 804. The fuse 818 is adapted to fail, or "blow," when the energy of electric current flowing through the fuse 818 exceeds a predetermined energy threshold. The energy threshold of the fuse 818 may be sufficiently large to permit the position signals generated by the tracking sensor 806 to flow through the fuse 818 to the first conductor 814 and to the second conductor 816. As a result, the fuse 818 remains intact when the tracking system 100 monitors the location of the tracking sensor 806 as the lead assembly 102 is implanted into the anatomy 106.

After the lead assembly 102 is implanted in the anatomy 106, an overcurrent pulse of electric current may be conducted through the isolation component 800 to blow the fuse 818. The overcurrent pulse includes electric current having an energy that exceeds the energy threshold of the fuse 818. The overcurrent pulse may be supplied by the IMD 104 or another electronic power source. The overcurrent pulse can be delivered as a stimulus pulse through the first conductor 814 and/or the second conductor 816 to the first electrode 802 and/or the second electrode 804. The fuse 818 blows when the overcurrent pulse reaches the fuse 818. The blown fuse 818 opens an electric circuit that includes the first conductor 814, the second conductor 816, the first electrode 802, and the second electrode 804. For example, the blown fuse 818 opens the circuit by interrupting or opening the conductive pathway between the first electrode 802 and the second electrode 804. The opened circuit prevents later stimulus pulses and/or electric signals from being conveyed between the electrodes 802, 804 and between the conductors 814, 816.

Figure 9:
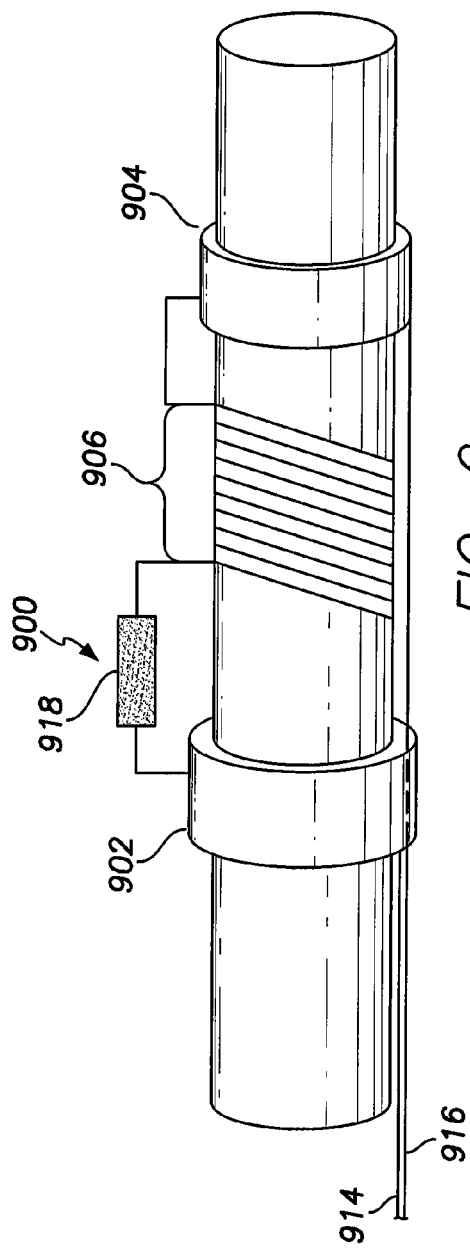
FIG. 9 is a circuit diagram of a fused electric isolation component and a tracking sensor in accordance with another embodiment.

FIG. 9 is a circuit diagram of a fused electric isolation component 900 and a tracking sensor 906 in accordance with another embodiment. The isolation component 900 may represent the isolation component 308 (shown in FIG. 3) and the tracking sensor 906 may represent the tracking sensor 300 (shown in FIG. 3). Similar to the isolation components 308, 500, 600, 700, 800 (shown in FIGS. 3, 5, 6, 7, and 8), the isolation component 900 is conductively coupled in series with the tracking sensor 906, a first electrode 902, a second electrode 904, a first conductor 914, and a second conductor 916.

The isolation component 900 includes a dissolving fuse 918 that is disposed between, and conductively coupled in series with, the electrodes 902, 904. The fuse 918 provides a conductive pathway between the tracking sensor 906 and the first electrode 902 (and between the first electrode 902 and the second electrode 904) during insertion of the lead assembly 102 into the anatomy 106. After the lead assembly 102 and the isolation component 900 is implanted into the anatomy 106, the fuse 918 may dissolve over a predetermined period of time. For example, the fuse 918 may be formed from a conductive material that dissolves when exposed to one or more fluids in the anatomy 106. When the fuse 918 dissolves, the fuse 918 opens an electric circuit that includes the first conductor 914, the second conductor 916, the first electrode 902, and the second electrode 904. For example, the dissolved fuse 918 is no longer present to provide a conductive pathway between the electrodes 902, 904. The opened circuit prevents later stimulus pulses and/or electric signals from being conveyed between the electrodes 902, 904 and between the conductors 914, 916.

Figure 10:
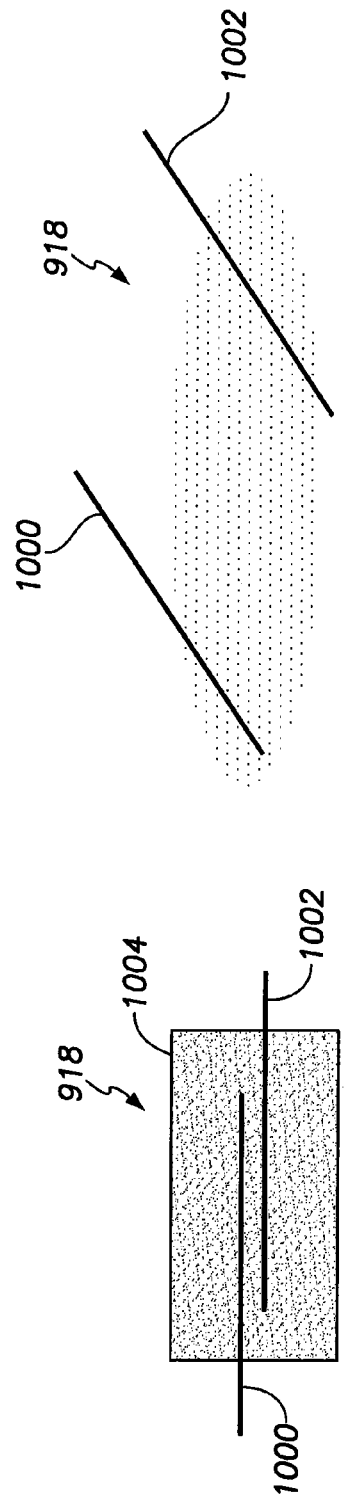
FIG. 10 is a schematic illustration of one embodiment of a dissolving fuse shown in FIG. 9.

FIG. 10 is a schematic illustration of one embodiment of the dissolving fuse 918. The fuse 918 includes conductors 1000, 1002 held near each other by a casing 1004. The conductors 1000, 1002 may be conductively coupled with the tracking sensor 906 (shown in FIG. 9) and one or more of the electrodes 902, 904 (shown in FIG. 9). For example, the conductor 1000 may be conductively coupled with the first electrode 902 and the conductor 1002 may be conductively coupled with the tracking sensor 906.

In one embodiment, the casing 1004 is formed from a conductive material that dissolves over a predetermined period of time when the casing 1004 is disposed within the anatomy 106. The conductors 1000, 1002 may be held apart from each other within the casing 1004 with the casing 1004 providing a conductive pathway between the conductors 1000, 1002. Alternatively, the casing 1004 may be non-conductive and the conductors 1000, 1002 may abut each other in the casing 1004 such that the casing 1004 holds the conductors 1000, 1002 together to form the conductive pathway therebetween.

The casing 1004 dissolves over a predetermined time period that the fuse 918 is exposed to one or more fluids in the anatomy 106. For example, the casing 1004 may be formed from mannitol or another sugar-based material that dissolves over a time period of several minutes to several hours following exposure to fluids in the anatomy 106. Alternatively, the casing 1004 may be formed from another type of material.

Figure 11:
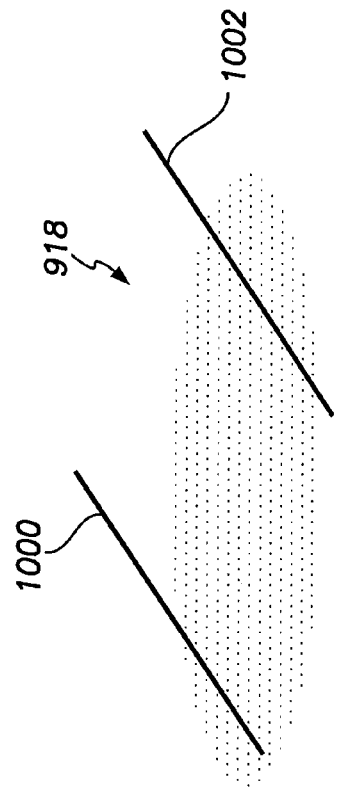
FIG. 11 is another schematic illustration of one embodiment of the dissolving fuse shown in FIG. 9.

FIG. 11 is a schematic illustration of one embodiment of the dissolving fuse 918 after the casing 1004 (shown in FIG. 10) has dissolved. As shown in FIG. 11, the conductors 1000, 1002 may be spaced apart from each other such that the conductors 1000, 1002 do not touch each other and no conductive pathway extends between the conductors 1000, 1002. The removal of the casing 1004 from the fuse 918 opens the circuit that extends through the conductors 1000, 1002 such that electric current (e.g., stimulus pulses and/or electric signals) cannot be conducted between the conductors 1000, 1002. As described above in connection with FIG. 9, when the fuse 918 opens, the conductive pathway between the first electrode 902 and the second electrode 904 is opened and electric current cannot flow between the electrodes 902, 904.

Figure 12:
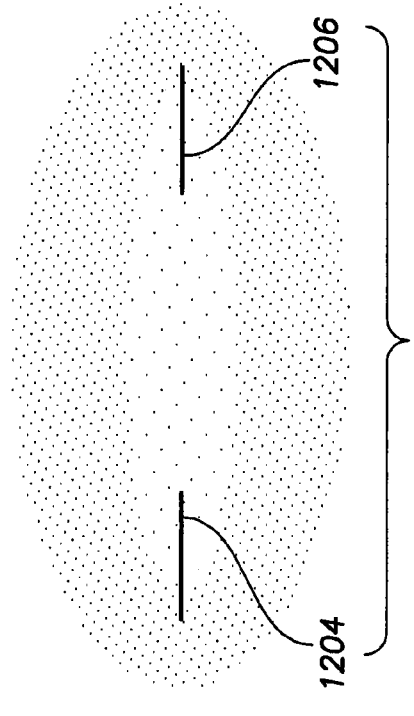
FIG. 12 is a schematic illustration of another embodiment of a dissolving fuse.

FIG. 12 is a schematic illustration of another embodiment of a dissolving fuse 1200. The fuse 1200 may be used in place of the fuse 918 shown in FIG. 9. The fuse 1200 includes a casing 1202 that is joined with conductors 1204, 1206. The conductor 1204 may be conductively coupled with the electrode 902 or 904 (shown in FIG. 9) and the conductor 1206 may be conductively coupled with the tracking sensor 906 (shown in FIG. 9). The casing 1202 includes an outer shell 1208 and a conductive core 1210. The conductive core 1210 is a conductive body that extends through the casing 1202 and is conductively coupled with the conductors 1204, 1206. The outer shell 1208 may be a non-conductive body, such as a layer of mannitol or another type of sugar. The conductive core 1210 may be a body that is capable of being dispersed within a human body. By way of example, the conductive core 1210 may be formed from gold microspheres or another type of metal or metal alloy composition of microspheres.

The conductive core 1210 provides a conductive pathway through the fuse 1200 between the conductors 1204, 1206. The casing 1202 holds the conductive core 1210 in place while the fuse 1200 is inserted into the anatomy 106. During insertion of the lead assembly 102, the conductive core 1210 provides a conductive pathway for the tracking sensor 906 (shown in FIG. 9) to convey position signals to the tracking system 100 along the first conductor 914 (shown in FIG. 9) and the second conductor 916 (shown in FIG. 9). After a predetermined time following exposure of the fuse 1200 to the fluids in the anatomy 106 and/or body, the casing 1202 dissolves and the conductive core 1210 is dispersed in the body or anatomy 106.

Figure 13:
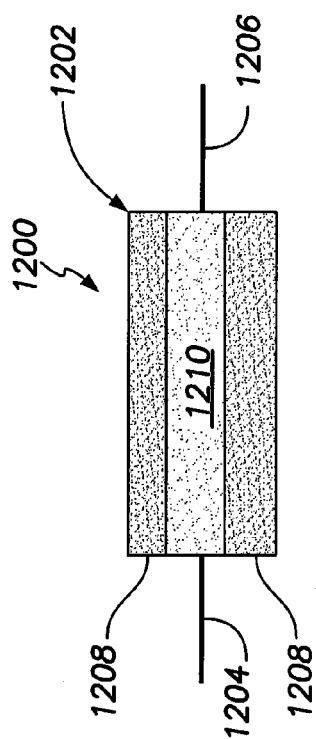
FIG. 13 is another schematic illustration of one embodiment of the dissolving fuse shown in FIG. 12.

FIG. 13 is a schematic illustration of one embodiment of the dissolving fuse 1200 after the casing 1202 (shown in FIG. 12) has dissolved and the conductive core 1210 (shown in FIG. 12) is dispersed. As shown in FIG. 13, the conductors 1204, 1206 may be spaced apart from each other such that the conductors 1204, 1206 do not touch each other and no conductive pathway extends between the conductors 1204, 1206 when the casing 1202 is dissolved and the conductive core 1210 is dispersed. The removal of the casing 1202 and conductive core 1210 opens the circuit that extends through the conductors 1204, 1206 such that electric current (e.g., stimulus pulses and/or electric signals) cannot be conducted between the conductors 1204, 1206. As described above in connection with FIG. 9, when the fuse opens, the conductive pathway between the first electrode 902 and the second electrode 904 is opened and electric current cannot flow between the electrodes 902, 904.

Figure 14:
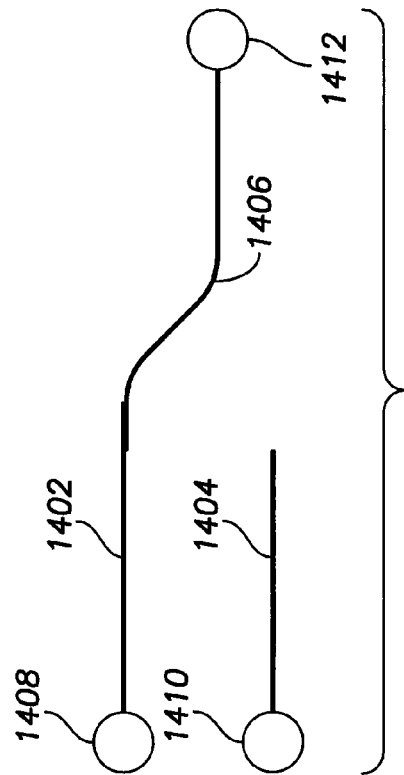
FIG. 14 is a schematic diagram of a switch mechanism in accordance with one embodiment.
Figure 15:
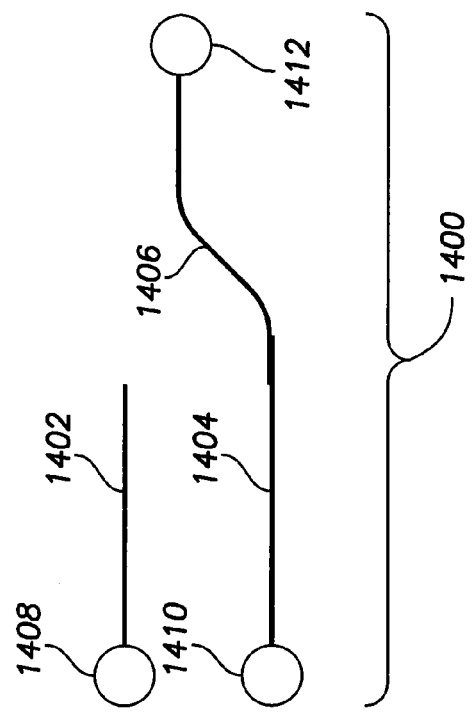
FIG. 15 is another schematic diagram of the switch mechanism shown in FIG. 14.

FIGS. 14 and 15 are schematic diagrams of a switch mechanism 1400 in accordance with one embodiment. The switch mechanism 1400 may be used conductively couple one of at least first and second conductors 1402, 1404 with a third conductor 1406. In one embodiment, the first conductor 1402 is conductively coupled with an electrode 1408 in the lead assembly 102, such as the electrode 210A. The second conductor 1404 may be conductively coupled with a position tracking sensor 1410, such as the tracking sensor 300. The third conductor 1406 may be conductively coupled with a conductive terminal 1412, such as one or more of the terminals 208 of the lead assembly 102.

The third conductor 1406 may be formed from a shape memory alloy that changes shape when heated. A shape memory alloy includes a conductive body that is associated with a transformation temperature. When the body is at a temperature that is below the transformation temperature, the body has a first shape. When the body is heated to a temperature that exceeds the transformation temperature, the shape of the body changes to a second shape. Subsequent cooling of the body can result in the shape of the body returning to the shape associated with temperatures below the transformation temperature.

In the embodiment shown in FIG. 14, the third conductor 1406 can be formed from a shape memory alloy that is heated to a temperature above the associated transformation temperature. The shape of the third conductor 1406 remains in the shape shown in FIG. 14 while the temperature of the third conductor 1406 remains above the transformation temperature. The second and third conductors 1404, 1406 may be positioned within the lead assembly 102 such that the second and third conductors 1404, 1406 are engaged with each other to provide a conductive pathway or circuit between the tracking sensor 1410 and the terminal 1412 when the third conductor 1406 is heated above the transformation temperature. The third conductor 1406 may be heated above the transformation temperature to conductively couple the tracking sensor 1410 with the terminal 1412 while the tracking system 100 monitors the location of the tracking sensor 1410 in the anatomy 106.

When the lead assembly 102 is implanted in the anatomy 106, the temperature of the third conductor 1406 may cool to below the transformation temperature. The cooling of the third conductor 1406 can cause the third conductor 1406 to change shape to the shape shown in FIG. 15. When the third conductor 1406 cools, the third conductor 1406 changes shape such that the third conductor 1406 is separated from the first conductor 1404, as shown in FIG. 15. The conductive pathway or circuit extending through the first and third conductors 1402, 1406 and that couples the tracking sensor 1410 with the terminal 1412 is opened when the third conductor 1406 changes shape.

Also as shown in FIG. 15, the cooling of the third conductor 1406 may cause the third conductor 1406 to change to a shape that causes the third conductor 1406 to contact or engage the second conductor 1404. The second and third conductors 1404, 1406 contact or engage each other to form a conductive pathway or circuit between the electrode 1408 and the terminal 1412 in the illustrated embodiment. The second and third conductors 1404, 1406 may remain in contact with each other as long as the third conductor 1406 is not heated above the transformation temperature. The transformation temperature can be sufficiently high that the normal operating temperatures to which the third conductor 1406 is exposed (e.g., the human body temperature) do not exceed the transformation temperature.

In another embodiment, the second conductor 1404 may be conductively coupled with another sensor or electronic component. For example, the second conductor 1404 may be coupled with an oxygen sensor, acoustic sensor, or other sensor. The third conductor 1406 may be heated above the transformation temperature to conductively couple the electronic component joined with the second conductor 1404 to the terminal 1412. The electronic component can communicate data signals, such as oxygen measurements, acoustic measurements, and the like, to the terminal 1412. The terminal 1412 can be conductively coupled with a monitoring device, such as the IMD 104 or another device that receives and analyzes the data signals from the electronic component.

The third conductor 1406 may be cooled to decouple the electronic component from the terminal 1412.

Figure 16:
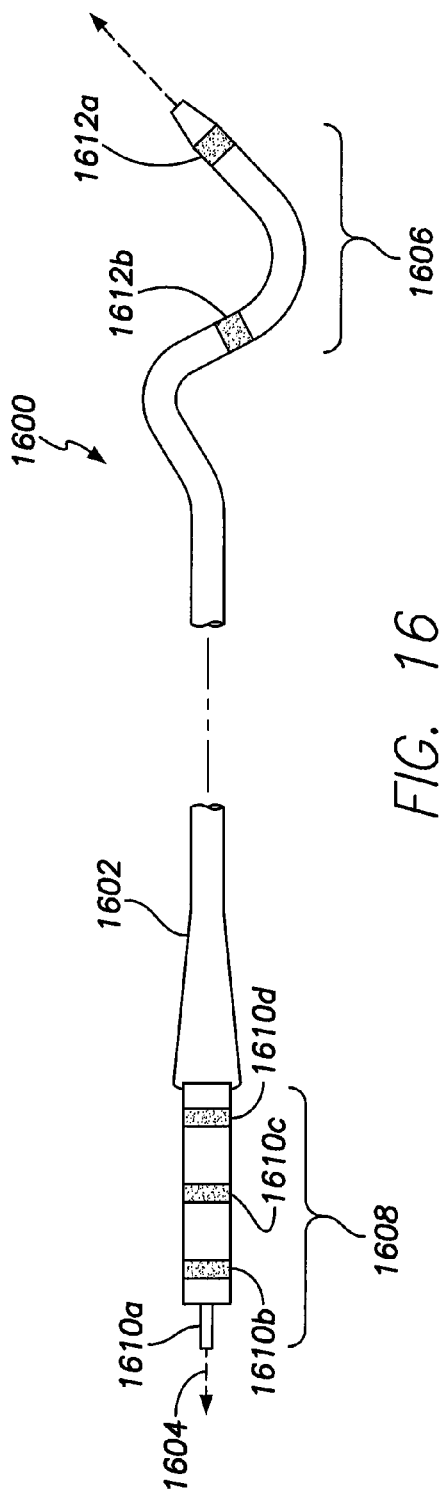
FIG. 16 is a perspective view of another embodiment of an implantable lead assembly.

FIG. 16 is a perspective view of another embodiment of an implantable lead assembly 1600. Similar to the lead assembly 102 shown in FIG. 1, the lead assembly 1600 includes an elongated tubular body 1602 extending along a center axis 1604 from a distal leading end 1606 to a proximal connector end 1608. The connector end 1608 includes several conductive terminals 1610A-D, such a pin contact 1610A and three ring contacts 1610B, 1610C, 1610D. The terminals 1610 are generally referred to by the reference number 1610 and are individually referred to by the reference number 1610A, 1610B, 1610C, or 1610D. While four terminals 1610A-D are shown, alternatively, a different number of one or more of the terminals 1610A-D may be provided.

The leading end 1606 of the lead assembly 1600 includes several conductive electrodes 1612A, 1612B. In the illustrated embodiment, the electrodes 1612A, 1612B include a tip electrode 1612A and a ring electrode 1612B. While two electrodes 1612A, 1612B are shown, alternatively, a different number and/or type of electrodes 1612A, 1612B may be provided. Similar to the electrodes 210, the electrodes 1612A, 1612B are disposed along an outer surface of the body 1602 in order to deliver stimulus pulses to the anatomy 106 and/or sense electric signals of the anatomy 106.

In the illustrated embodiment, there are fewer electrodes 1612A, 1612B than terminals 1610A-D. As described below, a subset of the terminals 1610A-D includes terminals that are conductively coupled with a position tracking sensor 1702 (shown in FIG. 17) while another, different, and non-overlapping subset of the terminals 1610A-D includes terminals that are conductively coupled with the electrodes 1612A, 1612B. For example, the terminals 1610A, 1610B may be conductively coupled with the electrodes 1612A, 1612B and while the terminals 1610C, 1610D are conductively coupled with the tracking sensor 300. The terminals 1610A, 1610B are dedicated to communicating stimulus pulses to, and/or receiving electric signals from, the electrodes 1612A, 1612B. The terminals 1610C, 1610D are dedicated to communicating position signals from the tracking sensor 1702 to a tracking system such as the tracking system 100 (shown in FIG. 1).

Figure 17:
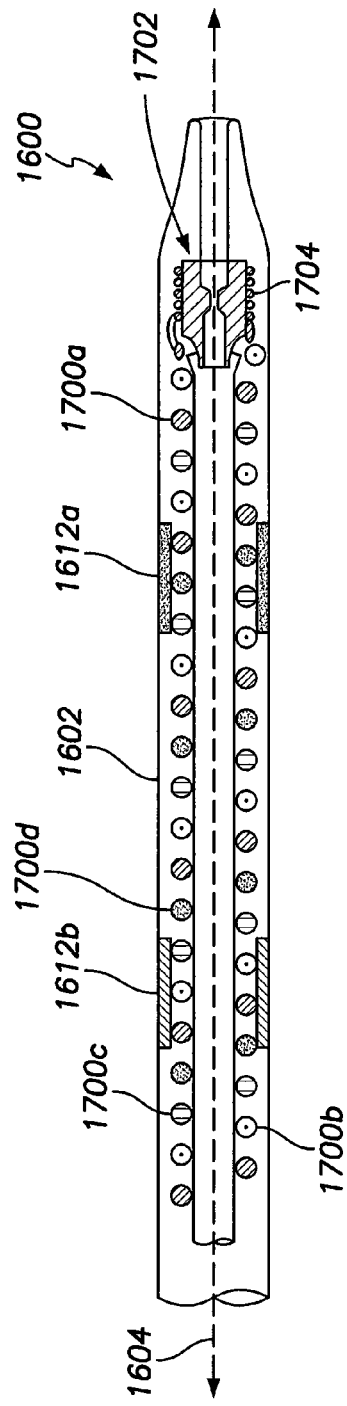
FIG. 17 is a cross-sectional view of a leading end of the lead assembly shown in FIG. 16 in accordance with one embodiment.

FIG. 17 is a cross-sectional view of the leading end 1606 of the lead assembly 1600 in accordance with one embodiment. Several elongated coiled conductors 1700A-D are disposed in the body 1602 and extend along the center axis 1604. The conductors 1700A-D may be similar to the conductors 306A-D (shown in FIG. 3). For example, the conductors 1700A-D may be separate (e.g., not conductively coupled) coils that are helically wrapped around the center axis 1604. The conductor 1700A is conductively coupled with the terminal 1610A (shown in FIG. 16) and the electrode 1612A to provide a conductive pathway or circuit therebetween. The conductor 1700B is conductively coupled with the terminal 1610B and the electrode 1612B to provide a conductive pathway or circuit therebetween.

The tracking sensor 1702 is disposed in the leading end 1606 of the body 1602 in a location that is distal to the electrodes 1612A, 1612B. Alternatively, the tracking sensor 1702 may be located between the electrodes 1612A, 1612B or proximal to the electrodes 1612A, 1612B. The tracking sensor 1702 may be similar to the tracking sensor 300. For example, the tracking sensor 1702 may generate electric current when the tracking sensor 1702 is exposed to external magnetic fields created by the tracking system 100. The electric current represents position signals indicative of the position of the tracking sensor 1702 relative to the tracking system 100.

The conductors 1700C, 1700D are conductively coupled with the tracking sensor 1702 and with the terminals 1610C, 1610D. For example, the tracking sensor 1702 may include a conductive coil 1704 that is coupled with the conductor 1700C and with the conductor 1700D. The conductor 1700C can be conductively coupled with the terminal 1610C and the conductor 1700D can be conductively coupled with the terminal 1610D. The conductors 1700C, 1700D convey position signals generated by the tracking sensor 1702 to the terminals 1610C, 1610D.

In the illustrated embodiment, each of the conductors 1700A-D is a dedicated conductor that communicates with a single electrode 1612 or the tracking sensor 1702, but not both and/or not with a plurality of electrodes 1612. For example, each of the conductors 1700A-D provides a conductive pathway or circuit between one of the terminals 1610A-D and one of the electrodes 1612A, 1612B or the tracking sensor 1702. The conductor 1700A provides a conductive pathway between the terminal 1610A and the electrode 1612A. The conductor 1700B provides a conductive pathway between the terminal 1610B and the electrode 1612B. The conductors 1700A, 1700B do not provide a conductive pathway between the tracking sensor 1702 and any terminal 1610A-D in the illustrated embodiment. Each of the conductors 1700C, 1700D provides a conductive pathway between a different terminal 1610C, 1610D and the tracking sensor 1702. In one embodiment, the conductors 1700C, 1700D do not provide a conductive pathway between a terminal 1610 and an electrode that delivers stimulus pulses to the anatomy 106.

The dedicated conductors 1700A-D may avoid the need for an electric isolation component, such as the isolation component 308 (shown in FIG. 3), coupled with a conductor 1700 between one or more of the electrodes 1612 and the tracking sensor 1702. For example, the isolation component 308 may not be needed to prevent electric signals and/or stimulus pulses to be conveyed between two or more electrodes 1612 by a single conductor 1700. Alternatively, the electric isolation component 308 may be coupled with one or more of the conductors 1700 in the embodiment shown in FIG. 17.

Figure 18:
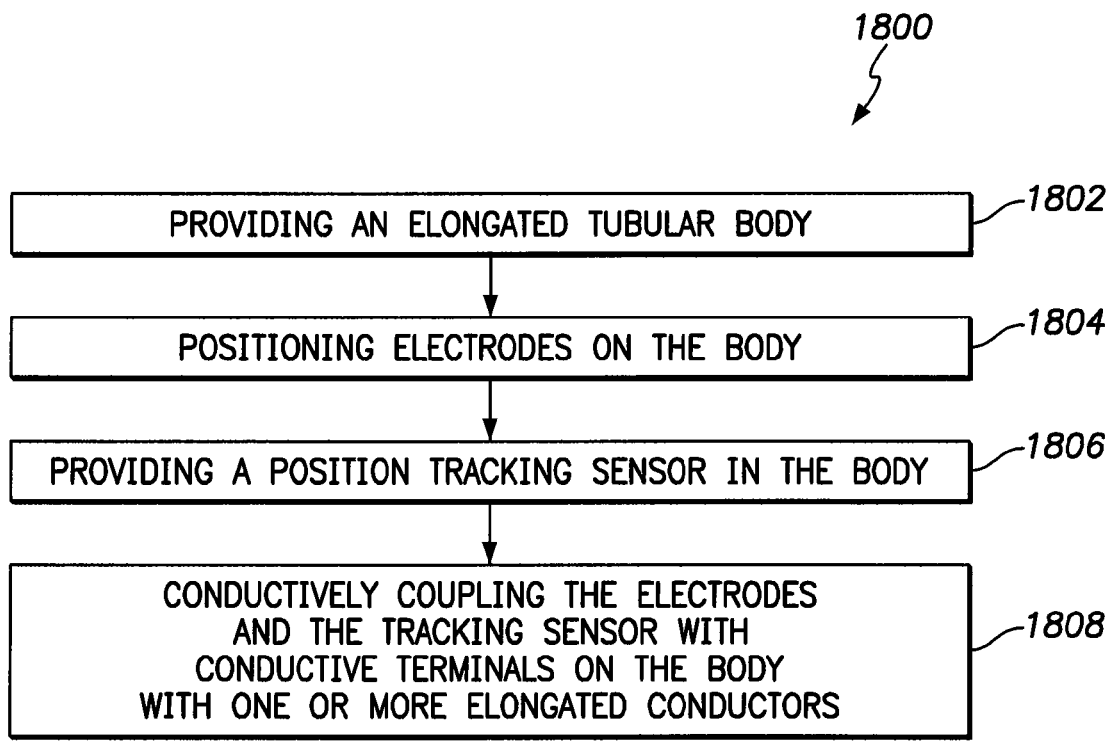
FIG. 18 is a flowchart of a method for manufacturing an implantable lead assembly of an implantable medical device in accordance with one embodiment.

FIG. 18 is a flowchart of a method 1800 for manufacturing an implantable lead assembly of an implantable medical device in accordance with one embodiment. The method 1800 may be used to manufacture or otherwise provide one or more embodiments of the lead assembly 102 or 1600 (shown in FIGS. 1 and 16).

At 1802, an elongated tubular body is provided. For example, the tubular body 200 or 1602 (shown in FIGS. 2 and 16) may be provided. The body includes elongated conductors, such as one or more of the conductors 306 or 1700 (shown in FIGS. 3 and 17), extending through the body. The body has a connector end, such as the connector end 206 or 1608 (shown in FIGS. 2 and 18), that mates with an implantable medical device (e.g., the IMD 104 shown in FIG. 1) and/or a tracking system (e.g., the tracking system 100 shown in FIG. 1). For example, the connector end may have one or more conductive terminals (e.g., terminals 208 or 1610 shown in FIGS. 2 and 16) at the connector end that mate with or otherwise engage corresponding contacts or terminals of the medical device and/or tracking system.

At 1804, one or more electrodes are positioned on the body. For example, one or more ring and/or tip electrodes (e.g., the electrodes 210 or 1612 shown in FIGS. 2 and 16) may be provided on an exterior surface of the body. The electrodes engage the anatomy when the lead assembly is implanted into the anatomy to deliver stimulus pulses to the anatomy and/or sense electric signals of the anatomy.

At 1806, a position tracking sensor is provided in the body. For example, the tracking sensor 300 or 1702 (shown in FIGS. 3 and 17) may be provided in a distal end of the body. The tracking sensor generates an electric position signal when the tracking sensor is exposed to an external magnetic field. For example, the tracking sensor may include a conductive coil in which an electric current is induced when the coil is exposed to a varying magnetic field. The current may be representative of a position of the tracking sensor in the magnetic field.

At 1808, the electrodes and tracking sensor are conductively coupled with the terminals of the body by one or more of the elongated conductors. In one embodiment, at least one of the conductors is a common conductor that is coupled with both an electrode and the tracking sensor. The tracking sensor may be conductively coupled with a plurality of the electrodes. As described above, an electric isolation component may be disposed in series between the electrodes or between the tracking sensor and at least one of the electrodes. The isolation component prevents electric signals and/or stimulus pulses from being conveyed between two electrodes through the tracking sensor. Alternatively, the tracking sensor and the electrodes may be conductively coupled with separate conductors.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Also, it is to be understood that phraseology and terminology used herein with reference to device or element orientation (such as, for example, terms like "central," "upper," "lower," "front," "rear," "distal," "proximal," and the like) are only used to simplify description of one or more embodiments described herein, and do not alone indicate or imply that the device or element referred to must have a particular orientation. In addition, terms such as "outer" and "inner" are used herein for purposes of description and are not intended to indicate or imply relative importance or significance.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments may be apparent to one of ordinary skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

Although the present invention has been described with reference to preferred embodiments, one of ordinary skill in the art will recognize that changes may be made in form and detail without departing from the spirit and scope of the invention.

What is claimed is:

1. A lead assembly of an implantable medical device, said lead assembly comprising:
    an elongated tubular body extending between a proximal connector end and a distal leading end, the body having a plurality of elongated conductors disposed in the body, the connector end of the body having a plurality of conductive terminals coupled with the conductors;
    a plurality of electrodes disposed on the body and configured to be located at or near an anatomy of interest of a patient, the plurality of electrodes being conductively coupled with the terminals of the body by the conductors, the electrodes configured to at least one of sense electric activity of the anatomy of interest or deliver stimulus pulses to the anatomy of interest;
    a position tracking sensor disposed in the body and conductively coupled with one or more of the terminals of the body by one or more of the conductors;
    a first and second electrode of the plurality of electrodes are conductively coupled with a first and second conductor of the plurality of elongated conductors, respectively, and the tracking sensor is conductively coupled in series with each of the first and second electrodes; and
    wherein the tracking sensor generates an electric position signal representative of a position of the tracking sensor when the body is being implanted into the patient.

2. The lead assembly of claim 1, wherein the tracking sensor includes a conductive coil disposed in the body closer to the distal end of the body than the electrode.

3. The lead assembly of claim 1, further comprising an electronic isolation component disposed in series with the first electrode, the second electrode, and the tracking sensor, the isolation component electrically isolating the first electrode from the second electrode by preventing stimulus pulses conveyed to the first electrode from flowing to the anatomy of interest through the second electrode or by preventing the electric activity sensed by the first electrode from being conveyed to the implantable medical device along the second conductor.

4. The lead assembly of claim 3, wherein the isolation component includes a resistor having an electric resistance characteristic that is greater than the electric resistance characteristic of any of the first electrode, the second electrode, or the tracking sensor.

5. The lead assembly of claim 3, wherein the isolation component includes a capacitor having an electric impedance characteristic that increases when the capacitor is exposed to the external magnetic field and decreases when the capacitor is removed from the external magnetic field.

6. The lead assembly of claim 3, wherein the isolation component includes a resistor and a capacitor disposed in series with the first electrode, the second electrode, and the tracking sensor.

7. The lead assembly of claim 3, wherein the isolation component includes an overcurrent protection fuse disposed between and in series with the first and second electrodes, the overcurrent protection fuse configured to fail and open a conductive pathway that conductively couples the first and second electrodes when an electric current of at least a threshold energy is conveyed through the fuse.

8. The lead assembly of claim 3, wherein the isolation component includes a dissolving fuse disposed between and in series with the first and second electrodes, the dissolving fuse configured to dissolve and open a conductive pathway that conductively couples the first and second electrodes after the dissolving fuse is disposed within the patient for at least a predetermined time period.

9. A lead assembly of an implantable medical device, said lead assembly comprising:
an elongated tubular body extending between a proximal connector end and a distal leading end, the body having first and second elongated conductors disposed in the body, the connector end of the body having first and second conductive terminals coupled with the first and second conductors, respectively;
first and second electrodes disposed on the body and configured to be located at or near an anatomy of interest of a patient, the first and second electrodes conductively coupled with the first and second terminals, respectively, by the first and second conductors, the first and second electrodes configured to at least one of sense electric activity of the anatomy of interest or deliver stimulus pulses to the anatomy of interest; and
a position tracking sensor disposed in the body and conductively coupled in series with the first and second electrodes, the tracking sensor configured to generate an electric signal that represents a position of the tracking sensor in the patient when the body is implanted in the patient, wherein the tracking sensor conductively couples the first and second electrodes when the body is being implanted into the patient.

10. The lead assembly of claim 9, wherein the tracking sensor includes a conductive coil disposed in the body closer to the distal end of the body than one or more of the first and second electrodes.

11. The lead assembly of claim 9, further comprising an electronic isolation component disposed in series with the first electrode, the second electrode, and the tracking sensor, the isolation component electrically isolating the first electrode from the second electrode by preventing stimulus pulses conveyed to the first electrode from flowing to the anatomy of interest through the second electrode or by preventing the electric activity sensed by the first electrode from being conveyed to the implantable medical device along the second conductor.

12. The lead assembly of claim 11, wherein the isolation component includes a resistor having an electric resistance characteristic that is greater than the electric resistance characteristic of any of the first electrode, the second electrode, or the tracking sensor.

13. The lead assembly of claim 11, wherein the isolation component includes a capacitor having an electric impedance characteristic that increases when the capacitor is exposed to the external magnetic field and decreases when the capacitor is removed from the external magnetic field.

14. The lead assembly of claim 11, wherein the isolation component includes a resistor and a capacitor disposed in series with the first electrode, the second electrode, and the tracking sensor.

15. The lead assembly of claim 11, wherein the isolation component includes an overcurrent protection fuse disposed between and in series with the first and second electrodes, the overcurrent protection fuse configured to fail and open a conductive pathway that conductively couples the first and second electrodes when an electric current of at least a threshold energy is conveyed through the fuse.

16. The lead assembly of claim 11, wherein the isolation component includes a dissolving fuse disposed between and in series with the first and second electrodes, the dissolving fuse configured to dissolve and open a conductive pathway that conductively couples the first and second electrodes after the dissolving fuse is disposed within the patient for at least a predetermined time period.

17. A method of manufacturing a lead assembly of an implantable medical device, said method comprising:
providing an elongated tubular body extending between a proximal connector end and a distal leading end, the body having first and second elongated conductors disposed in the body, the connector end of the body having first and second conductive terminals coupled with the first and second conductors, respectively;
positioning first and second electrodes on the body, the first and second electrodes configured to be located at or near an anatomy of interest of a patient, the first and second electrodes conductively coupled with the first and second terminals, respectively, by the first and second conductors, the first and second electrodes configured to at least one of sense electric activity of the anatomy of interest or deliver stimulus pulses to the anatomy of interest; and
providing a position tracking sensor in the body that conductively couples, in series, with the first and second electrodes, the tracking sensor configured to generate an electric signal that represents a position of the tracking sensor in the patient when body is in the patient, wherein the tracking sensor conductively couples the first and second electrodes when the body is implanted into the patient.

18. The method of claim 17, further comprising conductively coupling an electronic isolation component in series with the first electrode, the second electrode, and the tracking sensor, the isolation component electrically isolating the first electrode from the second electrode by preventing stimulus pulses conveyed to the first electrode from flowing to the anatomy of interest through the second electrode or by preventing the electric activity sensed by the first electrode from being conveyed to the implantable medical device along the second conductor.

19. The method of claim 18, wherein the isolation component includes a resistor having an electric resistance characteristic that is greater than the electric resistance characteristic of any of the first electrode, the second electrode, or the tracking sensor.

20. The method of claim 18, wherein the isolation component includes a capacitor having an electric impedance characteristic that increases when the capacitor is exposed to the external magnetic field and decreases when the capacitor is removed from the external magnetic field.

21. The lead assembly of claim 18, wherein the isolation component includes an overcurrent protection fuse disposed between and in series with the first and second electrodes, the overcurrent protection fuse configured to fail and open a conductive pathway that conductively couples the first and second electrodes when an electric current of at least a threshold energy is conveyed through the fuse.

22. The lead assembly of claim 18, wherein the isolation component includes a dissolving fuse disposed between and in series with the first and second electrodes, the dissolving fuse configured to dissolve and open a conductive pathway that conductively couples the first and second electrodes after the dissolving fuse is disposed within the patient for at least a predetermined time period.

* * * * *